US011318016B2

(12) United States Patent
Nieminen et al.

(10) Patent No.: US 11,318,016 B2
(45) Date of Patent: *May 3, 2022

(54) MITRAL VALVE ANNULOPLASTY DEVICE WITH TWISTED ANCHOR

(71) Applicant: Cardiac Dimensions Pty. Ltd., Kirkland, WA (US)

(72) Inventors: Gregory D. Nieminen, Bothell, WA (US); Garrett R. Beget, Bothell, WA (US); Nathan Aronson, Chico, CA (US); Lucas S. Gordon, Vashon, WA (US)

(73) Assignee: Cardiac Dimensions Pty. Ltd., Kirkland, WA (US)

( * ) Notice: Subject to any disclaimer, the term of this patent is extended or adjusted under 35 U.S.C. 154(b) by 206 days.

This patent is subject to a terminal disclaimer.

(21) Appl. No.: 16/573,903

(22) Filed: Sep. 17, 2019

(65) Prior Publication Data
US 2020/0253732 A1    Aug. 13, 2020

Related U.S. Application Data

(63) Continuation of application No. 15/368,467, filed on Dec. 2, 2016, now Pat. No. 10,449,048, which is a continuation of application No. 11/458,040, filed on Jul. 17, 2006, now Pat. No. 9,526,616, which is a continuation-in-part of application No. 10/742,585, filed on Dec. 19, 2003, now abandoned.

(51) Int. Cl.
*A61F 2/24* (2006.01)

(52) U.S. Cl.
CPC .......... *A61F 2/2451* (2013.01); *A61F 2/2442* (2013.01); *A61F 2/2466* (2013.01)

(58) Field of Classification Search
CPC ..... A61F 2/2451; A61F 2/2442; A61F 2/2466
See application file for complete search history.

(56) References Cited

U.S. PATENT DOCUMENTS

| 3,620,212 A | 11/1971 | Fannon, Jr. et al. |
| 3,786,806 A | 1/1974 | Johnson et al. |
| 3,890,977 A | 6/1975 | Wilson |

(Continued)

FOREIGN PATENT DOCUMENTS

| EP | 0893133 A1 | 1/1999 |
| EP | 0903110 A1 | 3/1999 |

(Continued)

OTHER PUBLICATIONS

El-Maasarany et al.; The coronary sinus conduit function: Anatomical study (relationship to adjacent structures); http://europace.oxfordjournals.org/cge/content/full/7/5/475. (accessed Sep. 9, 2008).

(Continued)

*Primary Examiner* — William H Matthews
(74) *Attorney, Agent, or Firm* — Shay Glenn LLP; Thomas M. Zlogar

(57) ABSTRACT

The present invention relates to a tissue shaping device adapted to be disposed in a vessel near a patient's heart to reshape the patient's heart. The device comprises a first anchor and a second anchor adapted to be deployed by a catheter to engage a vessel wall while the first anchor is adapted to resist the compression of a first part of the first anchor and resist the expansion of a second part of the first anchor in response to a compressive force on the first part.

8 Claims, 10 Drawing Sheets

(56) References Cited

U.S. PATENT DOCUMENTS

| | | |
|---|---|---|
| 3,974,526 A | 8/1976 | Dardik et al. |
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,099,838 A | 3/1992 | Bardy |
| 5,104,404 A | 4/1992 | Wolff |
| 5,197,978 A | 3/1993 | Hess |
| 5,250,071 A | 10/1993 | Palermo |
| 5,261,916 A | 11/1993 | Engelson |
| 5,265,601 A | 11/1993 | Mehra |
| 5,344,426 A | 9/1994 | Lau et al. |
| 5,350,420 A | 9/1994 | Cosgrove et al. |
| 5,411,549 A | 5/1995 | Peters |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,617,854 A | 4/1997 | Munsif |
| 5,662,703 A | 9/1997 | Yurek et al. |
| 5,676,671 A | 10/1997 | Inoue |
| 5,733,325 A | 3/1998 | Robinson et al. |
| 5,733,328 A | 3/1998 | Fordenbacher |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,001,118 A | 12/1999 | Daniel et al. |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,045,497 A | 4/2000 | Schweich, Jr. et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,159,220 A | 12/2000 | Gobron et al. |
| 6,162,168 A | 12/2000 | Schweich, Jr. et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,306,141 B1 | 10/2001 | Jervis |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,368,345 B1 | 4/2002 | Dehdashtian et al. |
| 6,395,017 B1 | 5/2002 | Dwyer et al. |
| 6,402,781 B1 | 6/2002 | Langberg et al. |
| 6,409,750 B1 | 6/2002 | Hyodoh et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,478,776 B1 | 11/2002 | Rosenman et al. |
| 6,503,271 B2 | 1/2003 | Duerig et al. |
| 6,537,314 B2 | 3/2003 | Langberg et al. |
| 6,556,873 B1 | 4/2003 | Smits |
| 6,562,066 B1 | 5/2003 | Martin |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,652,571 B1 | 11/2003 | White et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,798,231 B2 | 9/2004 | Iwasaki et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,827,690 B2 | 12/2004 | Bardy |
| 6,881,220 B2 | 4/2005 | Edwin et al. |
| 6,890,353 B2 | 5/2005 | Cohn et al. |
| 6,899,734 B2 | 5/2005 | Castro et al. |
| 6,908,478 B2 | 6/2005 | Alferness et al. |
| 6,908,482 B2 | 6/2005 | McCarthy et al. |
| 6,926,690 B2 | 8/2005 | Renati |
| 6,935,404 B2 | 8/2005 | Duerig et al. |
| 6,949,122 B2 | 9/2005 | Adams et al. |
| 6,955,689 B2 | 10/2005 | Ryan et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 7,004,958 B2 | 2/2006 | Adams et al. |
| 7,087,064 B1 | 8/2006 | Hyde |
| 7,128,073 B1 | 10/2006 | van der Burg et al. |

(56) References Cited

U.S. PATENT DOCUMENTS

| | | |
|---|---|---|
| 7,152,605 B2 | 12/2006 | Khairkhahan et al. |
| 7,175,653 B2 | 2/2007 | Gaber |
| 7,179,282 B2 | 2/2007 | Alferness et al. |
| 7,270,676 B2 | 9/2007 | Alferness et al. |
| 7,309,354 B2 | 12/2007 | Mathis et al. |
| 7,311,729 B2 | 12/2007 | Mathis et al. |
| 7,316,708 B2 | 1/2008 | Gordon et al. |
| 7,364,588 B2 | 4/2008 | Mathis et al. |
| 7,452,375 B2 | 11/2008 | Mathis et al. |
| 7,503,931 B2 | 3/2009 | Kowalsky et al. |
| 7,591,826 B2 | 9/2009 | Alferness et al. |
| 7,608,102 B2 | 10/2009 | Adams et al. |
| 7,635,387 B2 | 12/2009 | Reuter et al. |
| 7,674,287 B2 | 3/2010 | Alferness et al. |
| 7,758,639 B2 | 7/2010 | Mathis |
| 7,814,635 B2 | 10/2010 | Gordon |
| 7,828,841 B2 | 11/2010 | Mathis et al. |
| 7,828,842 B2 | 11/2010 | Nieminen et al. |
| 7,828,843 B2 | 11/2010 | Alferness et al. |
| 7,837,728 B2 | 11/2010 | Nieminen et al. |
| 7,837,729 B2 | 11/2010 | Gordon et al. |
| 7,887,582 B2 | 2/2011 | Mathis et al. |
| 7,955,384 B2 | 6/2011 | Rafiee et al. |
| 8,006,594 B2 | 8/2011 | Hayner et al. |
| 8,062,358 B2 | 11/2011 | Mathis et al. |
| 8,075,608 B2 | 12/2011 | Gordon et al. |
| 8,172,898 B2 | 5/2012 | Alferness et al. |
| 8,182,529 B2 | 5/2012 | Gordon et al. |
| 8,250,960 B2 | 8/2012 | Hayner et al. |
| 8,439,971 B2 | 5/2013 | Reuter et al. |
| 8,974,525 B2 | 3/2015 | Nieminen et al. |
| 9,320,600 B2 | 4/2016 | Nieminen et al. |
| 9,408,695 B2 | 8/2016 | Mathis et al. |
| 9,474,608 B2 | 10/2016 | Mathis et al. |
| 9,526,616 B2 | 12/2016 | Nieminen et al. |
| 9,597,186 B2 | 3/2017 | Nieminen et al. |
| 9,827,098 B2 | 11/2017 | Mathis et al. |
| 9,827,099 B2 | 11/2017 | Mathis et al. |
| 9,827,100 B2 | 11/2017 | Mathis et al. |
| 9,956,076 B2 | 5/2018 | Mathis et al. |
| 9,956,077 B2 | 5/2018 | Nieminen et al. |
| 10,052,205 B2 | 8/2018 | Mathis et al. |
| 10,166,102 B2 | 1/2019 | Nieminen et al. |
| 10,327,900 B2 | 6/2019 | Mathis et al. |
| 10,449,048 B2 | 10/2019 | Nieminen et al. |
| 10,456,257 B2 | 10/2019 | Mathis et al. |
| 10,456,259 B2 | 10/2019 | Mathis et al. |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0010507 A1 | 1/2002 | Ehr et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0161393 A1 | 10/2002 | Demond et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0193827 A1 | 12/2002 | McGuckin et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0093148 A1 | 5/2003 | Bolling et al. |
| 2003/0130730 A1 | 7/2003 | Cohn et al. |
| 2003/0135267 A1 | 7/2003 | Solem et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0172046 A1 | 9/2004 | Hlavka et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0260342 A1 | 12/2004 | Vargas et al. |
| 2004/0260384 A1 | 12/2004 | Allen |
| 2005/0004667 A1 | 1/2005 | Swinford et al. |
| 2005/0027351 A1 | 2/2005 | Reuter et al. |
| 2005/0033419 A1 | 2/2005 | Alferness et al. |
| 2005/0060030 A1 | 3/2005 | Lashinski et al. |
| 2005/0085903 A1 | 4/2005 | Lau |
| 2005/0096740 A1 | 5/2005 | Langberg et al. |
| 2005/0107810 A1 | 5/2005 | Morales et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0149182 A1 | 7/2005 | Alferness et al. |
| 2005/0177228 A1 | 8/2005 | Solem et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0271174 A1 | 11/2006 | Nieminen et al. |
| 2007/0066879 A1 | 3/2007 | Mathis et al. |
| 2007/0239270 A1 | 10/2007 | Mathis et al. |
| 2008/0015407 A1 | 1/2008 | Mathis et al. |
| 2008/0015679 A1 | 1/2008 | Mathis et al. |
| 2008/0015680 A1 | 1/2008 | Mathis et al. |
| 2010/0280602 A1 | 11/2010 | Mathis |
| 2011/0066234 A1 | 3/2011 | Gordon et al. |
| 2011/0106117 A1 | 5/2011 | Mathis et al. |
| 2012/0123532 A1 | 5/2012 | Mathis |
| 2012/0197389 A1 | 8/2012 | Alferness et al. |
| 2017/0189185 A1 | 7/2017 | Nieminen et al. |
| 2018/0256330 A1 | 9/2018 | Wypych |
| 2019/0262136 A1 | 8/2019 | Nieminen et al. |
| 2019/0336290 A1 | 11/2019 | Mathis et al. |
| 2019/0350708 A1 | 11/2019 | Mathis et al. |
| 2019/0365537 A1 | 12/2019 | Wypych |
| 2021/0298732 A1 | 9/2021 | Nieminen et al. |
| 2021/0330460 A1 | 10/2021 | Mathis et al. |
| 2021/0393403 A1 | 12/2021 | Nieminen et al. |

FOREIGN PATENT DOCUMENTS

| | | |
|---|---|---|
| EP | 0968688 A1 | 1/2000 |
| EP | 1050274 A1 | 11/2000 |
| EP | 1095634 A2 | 5/2001 |

(56) References Cited

FOREIGN PATENT DOCUMENTS

| | | |
|---|---|---|
| EP | 1177779 A2 | 2/2002 |
| EP | 2181670 A2 | 5/2010 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| SE | 9902455 | 12/2000 |
| WO | WO98/56435 A1 | 12/1998 |
| WO | WO00/44313 A1 | 8/2000 |
| WO | WO00/60995 A2 | 10/2000 |
| WO | WO00/74603 A2 | 12/2000 |
| WO | WO01/00111 A1 | 1/2001 |
| WO | WO01/19292 A1 | 3/2001 |
| WO | WO01/50985 A1 | 7/2001 |
| WO | WO01/54618 A1 | 8/2001 |
| WO | WO01/87180 A2 | 11/2001 |
| WO | WO02/00099 A2 | 1/2002 |
| WO | WO02/01999 A2 | 1/2002 |
| WO | WO02/05888 A1 | 1/2002 |
| WO | WO02/19951 A1 | 3/2002 |
| WO | WO02/34118 A2 | 5/2002 |
| WO | WO02/47539 A2 | 6/2002 |
| WO | WO02/053206 A2 | 7/2002 |
| WO | WO02/060352 A1 | 8/2002 |
| WO | WO02/062263 A2 | 8/2002 |
| WO | WO02/062270 A1 | 8/2002 |
| WO | WO02/062408 A2 | 8/2002 |
| WO | WO02/076284 A2 | 10/2002 |
| WO | WO02/078576 A2 | 10/2002 |
| WO | WO02/096275 A2 | 12/2002 |
| WO | WO03/015611 A2 | 2/2003 |
| WO | WO03/037171 A2 | 5/2003 |
| WO | WO03/049647 A1 | 6/2003 |
| WO | WO03/049648 A2 | 6/2003 |
| WO | WO03/055417 A1 | 7/2003 |
| WO | WO03/059198 A2 | 7/2003 |
| WO | WO03/063735 A2 | 8/2003 |
| WO | WO2004/045463 A2 | 6/2004 |
| WO | WO2004/084746 A2 | 10/2004 |
| WO | WO2005/046531 A2 | 5/2005 |
| WO | WO2005/058206 A1 | 6/2005 |

OTHER PUBLICATIONS

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents Induction of Atrial Fibrillation. Circulation. Sep. 16, 1997; 96(6): 1893-1898.

Pelton et al. Medical uses of nitinol; Material Science Forum; vols. 327-328; pp. 63-70; 2000 (held in Kanazawa, Japan, May 1999).

Pijls et al.; Measurement of fractional flow reserve to assess the functional severity of coronary-artery stenoses; The New England J. of Med.; vol. 334; No. 26; pp. 1703-1708; Jun. 27, 1996.

Pai, Suresh; U.S. Appl. No. 60/329,694 entitled "Percutaneous cardiac support structures and deployment means," filed Oct. 16, 2001.

Yamanouchi, et al.; Activation Mapping from the coronary sinus may be limited by anatomic variations; vol. 21 pp. 2522-2526; Nov. 1998.

Nieminen et al.; U.S. Appl. No. 16/568,055 entitled "Mitral valve annuloplastydevice with twisted anchor," filed Sep. 11, 2019.

Mathis et al.; U.S. Appl. No. 16/576,025 entitled "Tissue shaping device," filed Sep. 19, 2019.

MITRAL VALVE ANNULOPLASTY DEVICE WITH TWISTED ANCHOR

CROSS-REFERENCE TO RELATED APPLICATIONS

This application is a continuation of U.S. application Ser. No. 15/368,467, filed Dec. 2, 2016 which is a continuation of U.S. application Ser. No. 11/458,040, filed Jul. 17, 2006, now U.S. Pat. No. 9,526,616 (issued Dec. 27, 2016) which is a continuation-in-part of U.S. application Ser. No. 10/742,585, filed Dec. 19, 2003, now abandoned, each of which are incorporated herein by reference in its entirety and to which applications we claim priority under 35 USC § 120.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

This invention relates generally to devices and methods for shaping tissue by deploying one or more devices in body lumens adjacent to the tissue. One particular application of the invention relates to a treatment for mitral valve regurgitation through deployment of a tissue shaping device in the patient's coronary sinus or great cardiac vein.

The mitral valve is a portion of the heart that is located between the chambers of the left atrium and the left ventricle. When the left ventricle contracts to pump blood throughout the body, the mitral valve closes to prevent the blood being pumped back into the left atrium. In some patients, whether due to genetic malformation, disease or injury, the mitral valve fails to close properly causing a condition known as regurgitation, whereby blood is pumped into the atrium upon each contraction of the heart muscle. Regurgitation is a serious, often rapidly deteriorating, condition that reduces circulatory efficiency and must be corrected.

Two of the more common techniques for restoring the function of a damaged mitral valve are to surgically replace the valve with a mechanical valve or to suture a flexible ring around the valve to support it. Each of these procedures is highly invasive because access to the heart is obtained through an opening in the patient's chest. Patients with mitral valve regurgitation are often relatively frail thereby increasing the risks associated with such an operation. A device to perform mitral valve annuloplasty is therefore needed that can be implanted percutaneously without opening the chest wall.

SUMMARY OF THE DISCLOSURE

One aspect of the invention provides a tissue shaping device (such as a percutaneous mitral valve annuloplasty device) adapted to be deployed in a vessel to reshape tissue adjacent the vessel. The device comprises a first anchor and a second anchor adapted to be deployed by a catheter to engage a vessel wall, wherein the first anchor includes a shaping feature adapted to resist the compression of a first part of the first anchor and resist the expansion of a second part of the first anchor in response to a compressive force on the first part, and a support structure disposed between and operatively connecting the first anchor and the second anchor. In some embodiments the anchors are adapted to engage a coronary sinus.

In some embodiments the first anchor comprises two entwisted wire segments, possibly arranged in a figure-8 configuration having first and second arms coupled at at least one coupling point (formed from, e.g., entwisted wire) as the shaping feature. In some embodiments, the coupling point is substantially at an apex of the first anchor when the anchor is in its deployed configuration. In some embodiments, the anchor's width is greater than its height in its deployed configuration.

In some embodiments the device also includes an anchor lock adapted to lock the first anchor and/or the second anchor in an expanded configuration. In some embodiments the device has a coupler, which may include a tether and a hitch wire, which is adapted to couple the device to a delivery tool. In some embodiments the coupler is further adapted to release the device from the delivery tool. In some embodiments the device is adapted to be recaptured by the catheter.

One aspect of the invention is a method of performing mitral valve annuloplasty on a patient's heart. The method comprises percutaneously delivering a mitral valve annuloplasty device to a vessel in the patient's heart, where the device comprises first and second anchors and a support structure disposed between and operatively connecting the first and second anchors, anchoring the first anchor of the mitral valve annuloplasty device in the vessel, resisting compression of a first part of the first anchor and resisting expansion of a second part of the first anchor in response to a compressive force on the first part, and anchoring the second anchor of the mitral valve annuloplasty device.

In some embodiments the first anchoring step comprises expanding the first anchor from a delivery configuration to a deployed configuration in which the first anchor engages the coronary sinus. In some embodiments, the anchor's width in the deployed configuration is greater than its height. In some embodiments the method includes locking the first anchor in the deployed configuration.

In some embodiments of the method the second anchoring step includes expanding the second anchor from a delivery configuration to a deployed configuration in which the second anchor engages the coronary sinus. In some embodiments the method includes locking the second anchor in the deployed configuration.

In some embodiments the method includes capturing the first anchor and/or the second anchor within the catheter after the first anchoring step. The capturing step may include advancing a catheter distally over the anchor to place the anchor inside the catheter in the delivery configuration.

In some embodiments the method includes applying a proximally directed force on the mitral valve annuloplasty device after the first anchoring step. In some embodiments the method includes uncoupling the device from a delivery tool after the second anchoring step. The uncoupling may comprise releasing a hitch wire from the device and removing a tether from the device.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present invention relates to a medical device and uses thereof that supports or changes the shape of tissue near a vessel in which the device is placed. The present invention is particularly useful in reducing mitral valve regurgitation by changing the shape of or supporting a mitral valve annulus. In preferred embodiments, the device comprises a distal anchor adapted to be anchored in the coronary sinus which resists a compression of a distal part of the anchor and an expansion of a proximal part of the anchor in response to a compressive force on the distal part of the anchor. As used herein, "coronary sinus" refers to not only the coronary sinus itself, but also to the venous system associated with the coronary sinus, including the great cardiac vein.

Figure 1:
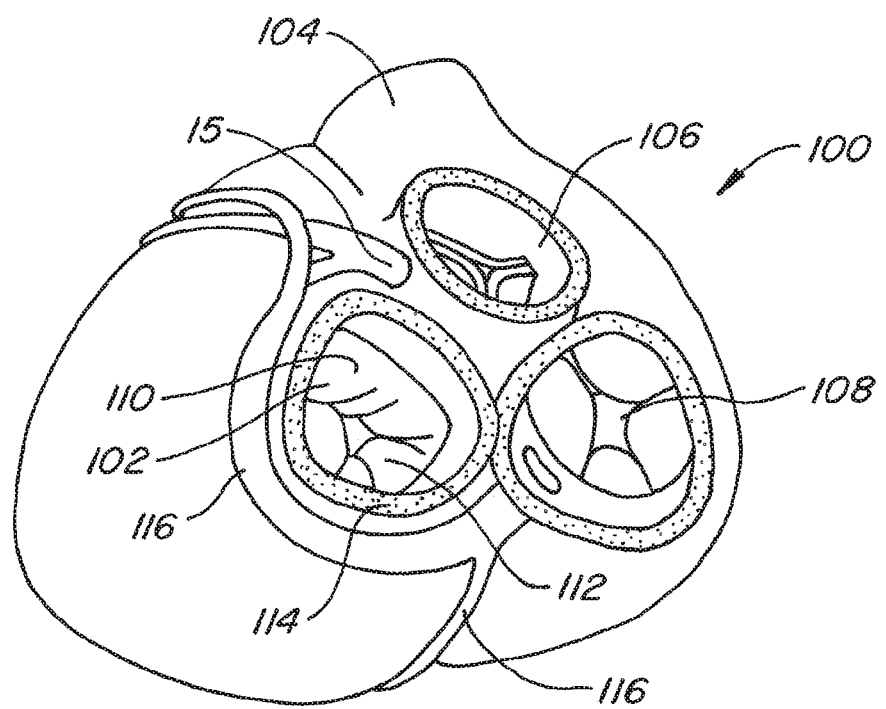
FIG. 1 is a superior view of a heart with the atria removed.

FIG. 1 is a superior view of a heart 100 with the atria removed. As pictured, the heart comprises several valves including mitral valve 102, pulmonary valve 104, aortic valve 106 and tricuspid valve 108. Mitral valve 102 includes anterior cusp 110, posterior cusp 112 and annulus 114. Annulus 114 encircles cusps 110 and 112 and functions to maintain their respective spacing to ensure complete mitral valve closure during left ventricular contractions of the heart 100. As illustrated, coronary sinus 116 partially encircles mitral valve 102 and is adjacent to mitral valve annulus 114. Coronary sinus 116 is part of the venous system of heart 100 and extends along the AV groove between the left atrium and the left ventricle. This places coronary sinus 116 essentially within the same plane as mitral valve annulus 114, making coronary sinus 116 available for placement of shaping device 200 in order to reshape mitral valve geometry and to restore proper valve function.

Figure 2:
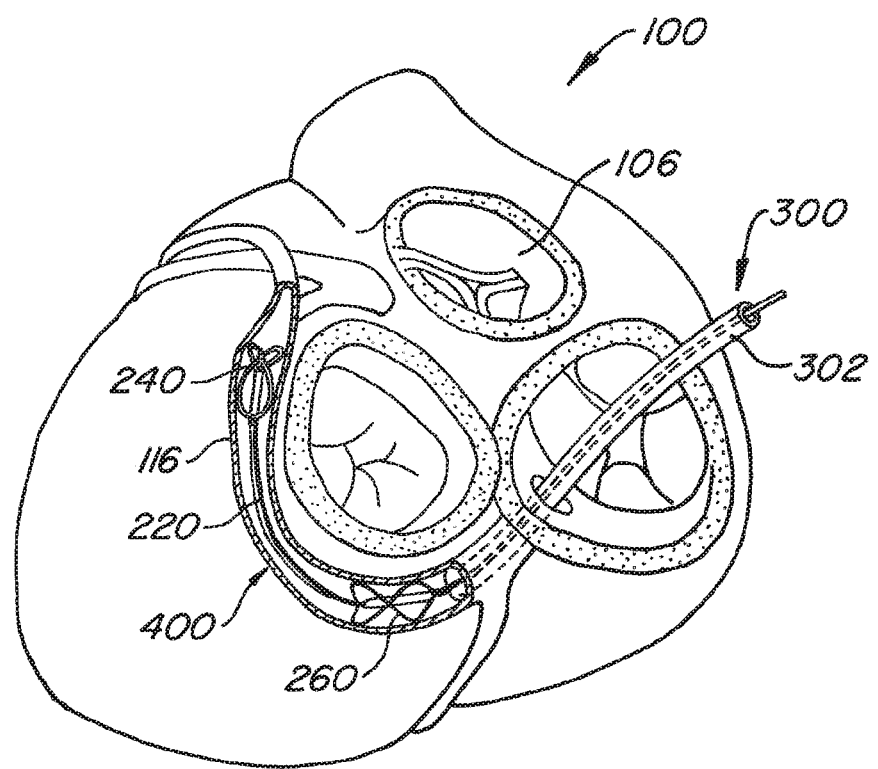
FIG. 2 illustrates one embodiment of an intravascular device deployed in a coronary sinus.

FIG. 2 illustrates one possible embodiment of an intravascular tissue shaping device 400 which is deployable in coronary sinus 116. As illustrated in FIG. 2, device 400 generally comprises an elongated connector 220 disposed between a distal anchor 240 and a proximal anchor 260. Both distal anchor 240 and proximal anchor 260 are shown in their deployed, or expanded, configurations, securely positioned within the coronary sinus 116. FIG. 2 further depicts, in phantom, a delivery tool 300 comprising catheter 302 for delivering and positioning intravascular device 400 in the coronary sinus 116.

Figure 3:
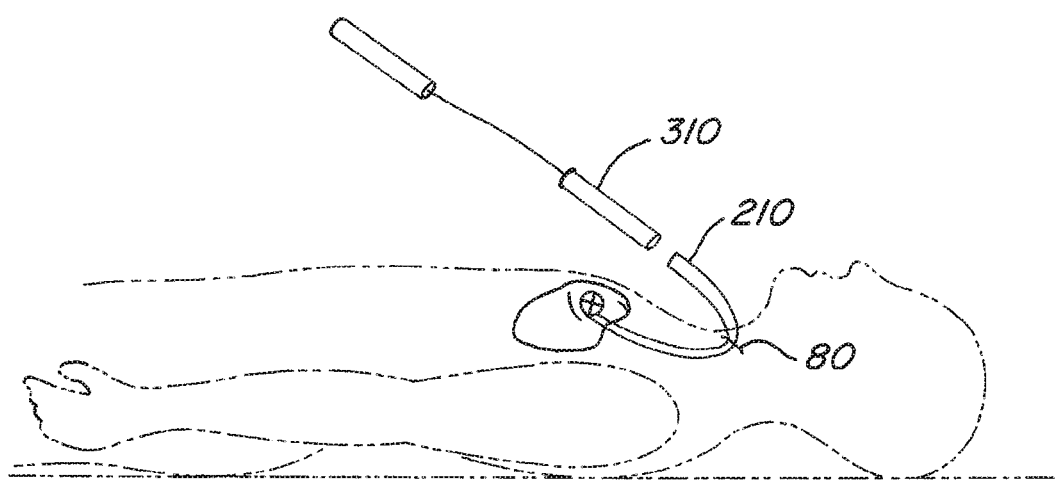
FIG. 3 illustrates one embodiment of delivering an intravascular device to a desired location within a patient's body.

FIG. 3 illustrates one embodiment of delivering the intravascular device of the present invention to a desired location within a patient's body. An incision 80 is made in the patient's skin to gain access to a blood vessel. The blood vessel may be, for example, the jugular vein. A guide catheter 210 is advanced through the patient's vasculature until its distal end is positioned near the desired location for the intravascular device. After positioning the guide catheter 210, a delivery catheter and advancing mechanism 310 are inserted through the guide catheter 210 to deploy the intravascular device at the desired location in the patient's body. In preferred embodiments, the delivery catheter is advanced until its distal end is inside the coronary sinus.

Figure 4:
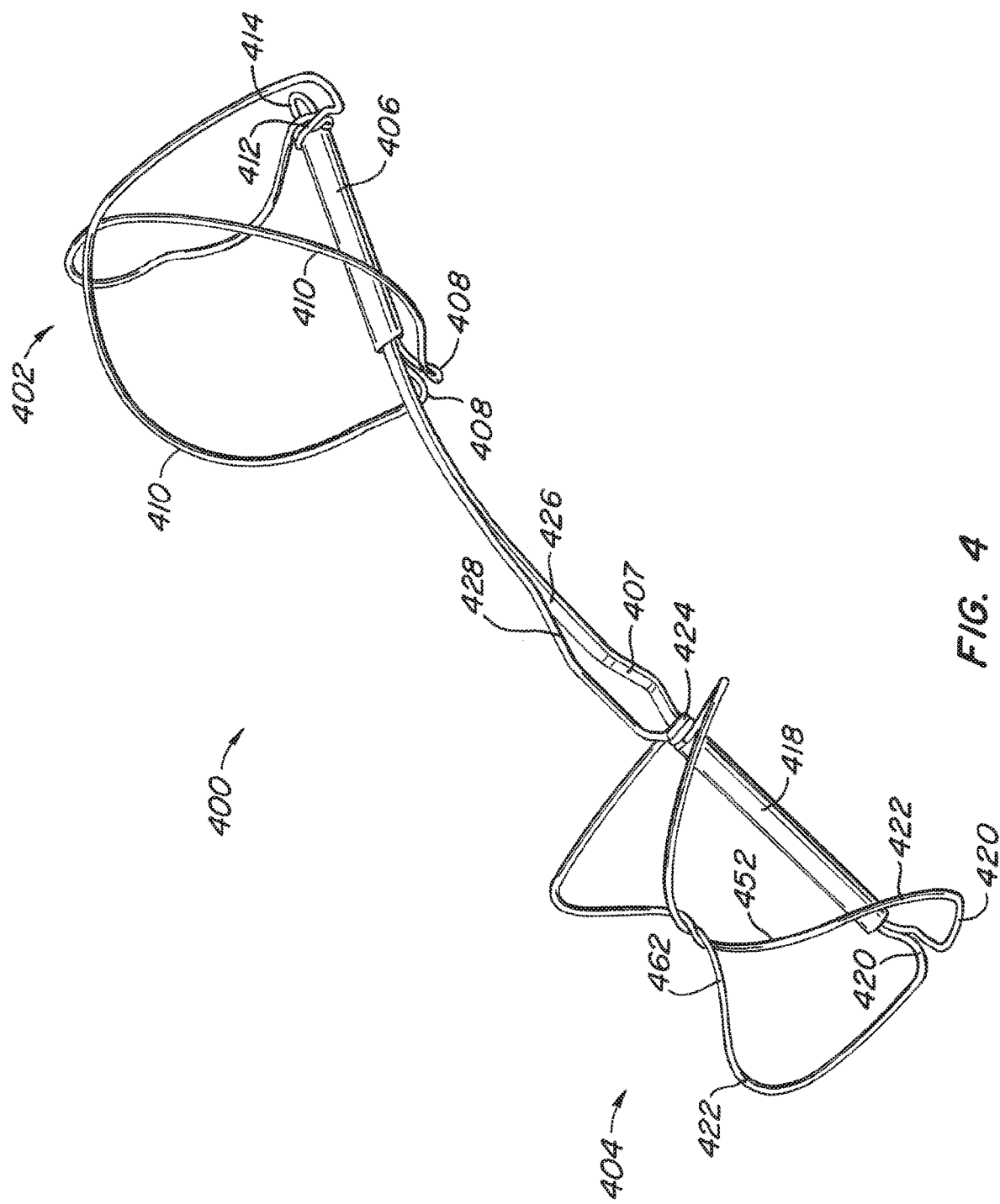
FIG. 4 shows one embodiment of an intravascular device with proximal anchor and distal anchor in their expanded and locked configurations.

FIG. 4 shows one embodiment of an intravascular shaping device 400 with proximal anchor 402 and distal anchor 404 in their expanded and locked configurations. In this embodiment, proximal anchor 402 is made from a shape memory metal wire, for example Nitinol, extending from a crimp 406. Stress relief portions 408 of the wire extend distal to crimp 406. The wire extends upward from stress relief portions 408 to form vessel engagement portions 410 which cross to form a figure-8 pattern, as shown. Vessel engagement portions 410 and crimp 406 engage the inner wall of the coronary sinus or other vessel in which the device is implanted. The vessel may be a superior vena cava as described in U.S. application Ser. No. 11/279,352, filed Apr. 11, 2006, now U.S. Pat. No. 7,503,932. The wire also forms a lock loop 412 which interacts with an arrowhead-shaped element 414 extending from the proximal end of the crimp to form the proximal anchor lock. The proximal side of proximal anchor 402 may be provided with variable slope recapture features, as described in U.S. patent application Ser. No. 10/429,172, filed May 2, 2003.

Likewise, the distal anchor is made from a shape memory wire extending from a crimp 418. Stress relief portions 420 of the wire extend distal to crimp 418. The wire extends upward from stress relief portions 420 to form vessel engagement portions 422 which twist around one another, which is described in further detail below. Vessel engagement portions 422 and crimp 418 engage the inner wall of the coronary sinus or other vessel in which the device is implanted. The wire also forms a lock loop 424. A bent portion 407 of connector 426 interacts with wire portion 428 and lock loop 424 to form a distal anchor lock to secure the distal anchor in an expanded configuration. Actuation of the proximal and distal anchor locks is further described in U.S. application Ser. No. 10/946,332, now U.S. Pat. No. 7,837,729, and U.S. application Ser. No. 10/945,855, now U.S. Pat. No. 8,182,529.

Extending between anchors 402 and 404 are a substantially flat connector 426 and a wire connector 428. In this embodiment, connectors 426 and 428 are both made of shape memory metal, such as Nitinol. By spanning the distance between proximal anchor 402 and distal anchor 404, connectors 426 and 428 maintain the reshaping force on the tissue.

Fatigue resistant and stress relief characteristics of the connector 426 and stress relief elements 420 and 408 are described in U.S. application Ser. No. 11/275,630, filed Jan. 19, 2006, now U.S. Pat. No. 7,351,260.

Prior to use, tissue shaping devices such as those shown in FIG. 4 may be stored in cartridges or other containers, such as described in U.S. application Ser. No. 10/946,332, now U.S. Pat. No. 7,837,729, and U.S. application Ser. No. 10/945,855, now U.S. Pat. No. 8,182,529, then delivered to the coronary sinus or other vessel in a delivery catheter, as shown in FIG. 2.

As shown in FIG. 4, the wire forming the distal anchor 404 has one end positioned within crimp 418. After exiting the distal end of the crimp, a first wire segment 452 of the distal anchor extends distally from the distal crimp, then bends radially outward from the longitudinal axis of the crimp. The wire then bends back proximally and radially inward where it twists around a second wire segment 462 at a coupling point substantially at the anchor's apex. The wire then wraps around the connectors 426 and 428 to form distal lock loop 424 before extending radially outwards and distally where it becomes the second wire segment 462. Finally, the second wire segment 462 bends proximally into the distal end of the distal crimp 418.

As can be seen in FIGS. 1 and 2, the location of the coronary sinus in which the distal anchor may be deployed may be tapered as the diameter along the length of the vessel decreases. Branching vessels may also contribute to a non-uniform diameter of the coronary sinus. Thus, the diameter of the coronary sinus where the distal part of the distal anchor contacts the coronary sinus wall may be narrower than the diameter where the proximal part of the distal anchor contacts the coronary sinus wall. Thus, the vessel wall may exert a larger compressive force on the distal part of the anchor than on the proximal part when the anchor is in a deployed configuration. This compressive force may cause compression of the distal end of the anchor, which can be transferred through the anchor and cause an expansion in a proximal part of the anchor. When such a compression occurs in the distal part, the distal anchor may not be able to anchor properly in the vessel. The distal anchor may compress and deform such that the amount of strain on the vessel is not great enough to allow the distal anchor to remain anchored in place.

Figure 5:
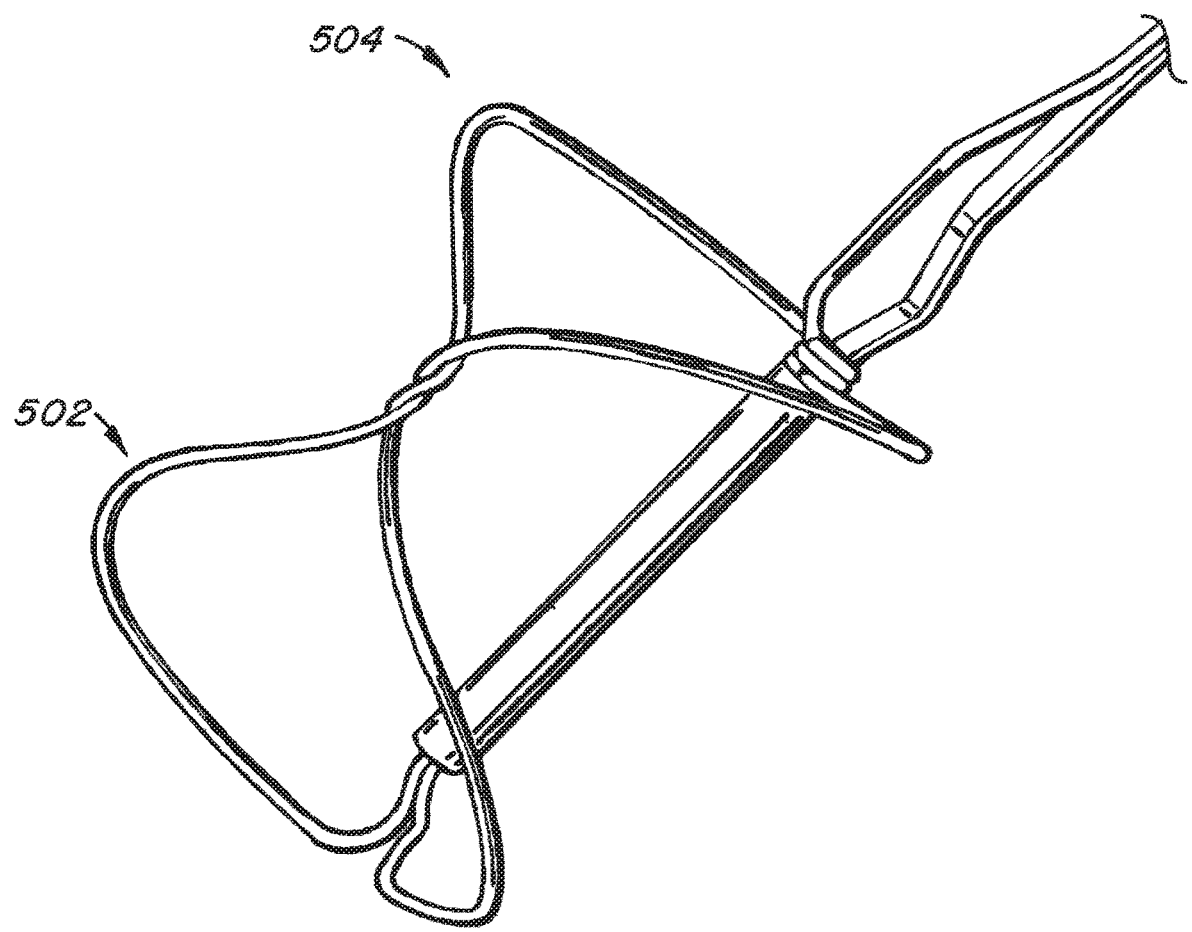
FIG. 5 shows details of the distal anchor of FIG. 4 with a shaping feature of two entwisted wire segments.

The exemplary embodiment shown in FIGS. 4 and 5 illustrates a device with an anchor shaping feature adapted to resist a compressive force exerted on a distal part of an anchor and resisting an expansion of a proximal part of the anchor in response to a compressive force on the distal part. The device of the present invention resists this compressive force on the distal part of the anchor and allows the device to anchor in place. Particularly, the distal anchor maintains a strain on the vessel which allows for the device to be anchored in the vessel to reduce mitral valve regurgitation, as described below.

As shown in FIG. 5, the distal anchor resists compression of its distal part 502 and resists expansion of its proximal part 504 in response to a compressive force on the distal part 502 of the anchor. Stated alternatively, coupling of the anchor's arms via the twisted wire as shown acts to prevent a compressive force exerted on the distal part of the anchor from being transmitted through the anchor into the proximal part of the anchor. The twist resists a distally exerted compressive force by creating a resistance to such a force.

While the anchor as described thus far resists a compressive force on the distal part of the anchor, the anchor as adapted may also resist a compressive force on the proximal part of the anchor by creating a resistance when a compressive force is exerted on the proximal part of the anchor. Similarly, the proximal anchor of an intravascular device may also be adapted to resist compressive forces from a vessel in which it might be deployed.

While the exemplary embodiments in FIGS. 4 and 5 show one full twist of the two segments of the distal anchor, it is understood that a different number of twists may be used to carry out the intent of the invention and the number of twists shown is not a limitation. In addition, it may be desirable to have a distal anchor with more than two entwisted segments, such as three, four, or more. Furthermore, anchor shaping features other than entwisted wires may be used.

In some embodiments the anchor's width (e.g., the maximum distance between anchor arms 422 in FIG. 4) may be greater than its height (e.g., the distance between crimp 418 and the twisted wire of anchor 404). For example, in some embodiments the distal anchor may be about 14 mm high and about 17 mm wide. The height and size may, however, vary while still carrying out the purposes of the invention.

Figure 6:
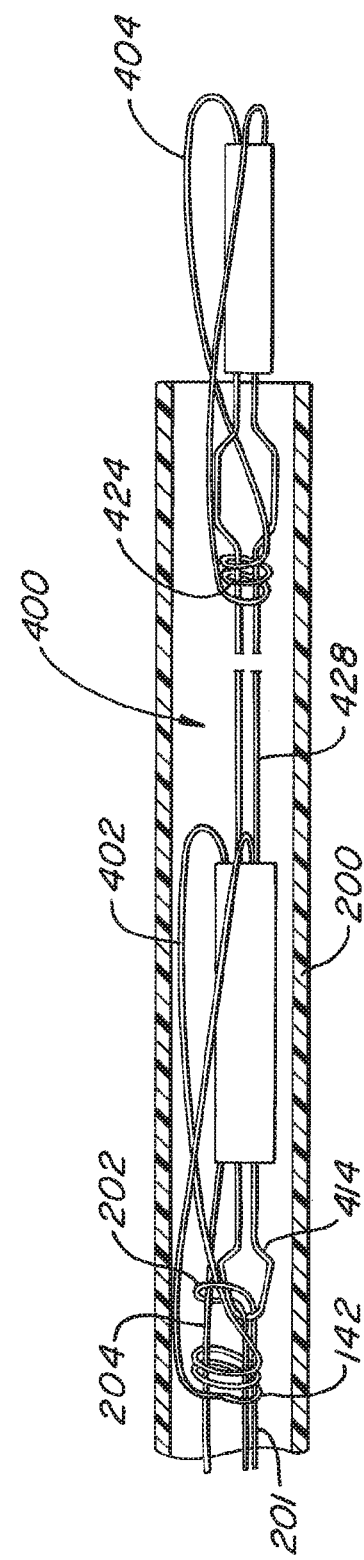
FIG. 6 illustrates an exemplary coupler that may be used with an intravascular device.

In some embodiments the intravascular device comprises a coupler adapted to couple the intravascular device to a delivery tool. FIG. 6 illustrates an exemplary coupler in use with a different intravascular device that may be used with the intravascular device of this invention. The coupler comprises a loop 202 at the end of tether 201 and a hitch wire 204. Loop 202 extends through arrowhead-shaped element 414, and the hitch wire 204 passes through loop 202 and into the crimp, thereby preventing loop 202 from being withdrawn from arrowhead-shaped element 414.

Figure 7:
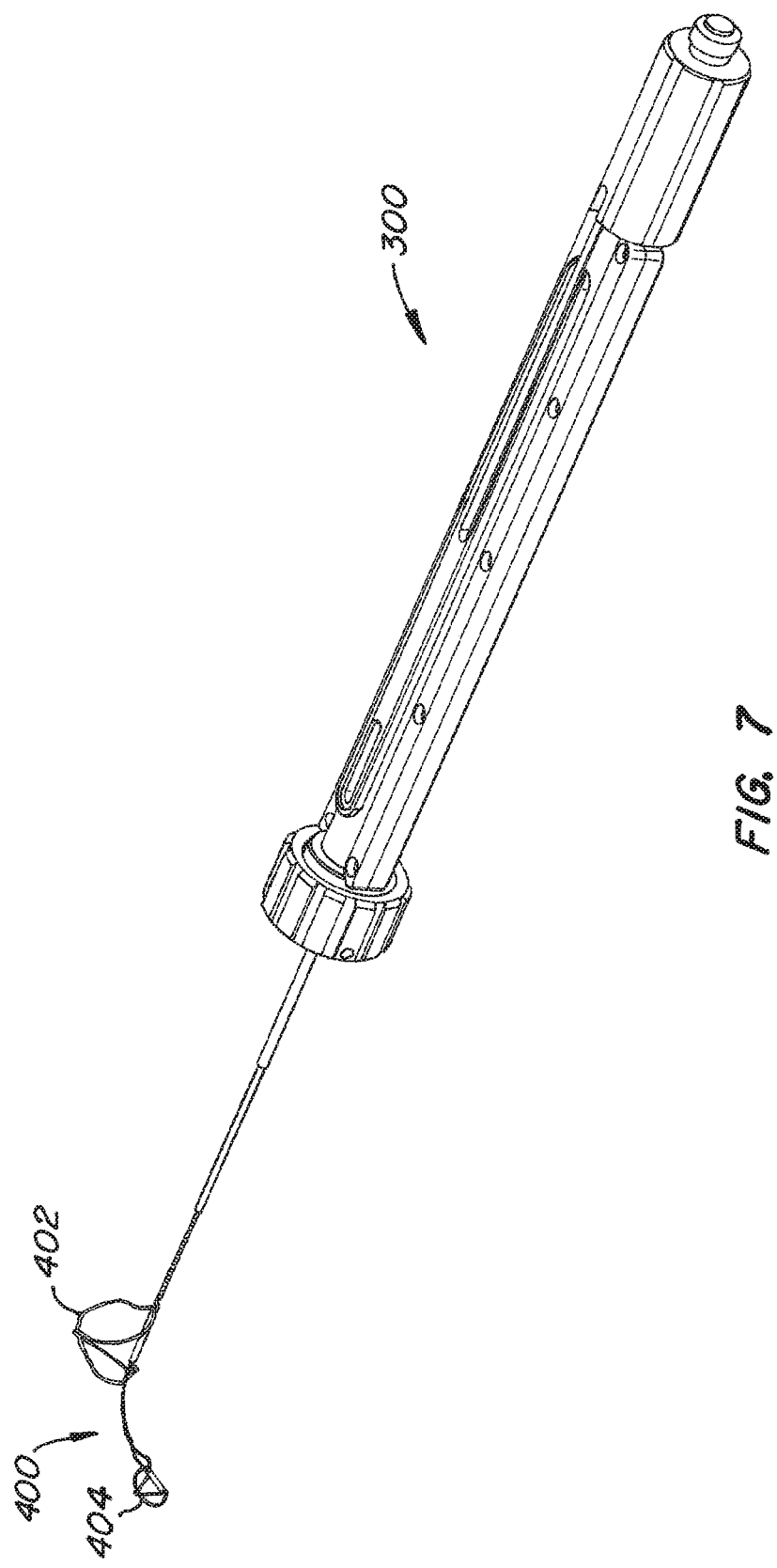
FIG. 7 shows an exemplary delivery tool that may be used to deliver and deploy an intravascular device.

FIG. 7 shows an exemplary delivery tool 300 that may be used to deliver and deploy an intravascular device 400 via a catheter (not shown). Details of the operation of delivery tool 300 may be found in U.S. patent application Ser. No. 10/946,332, filed Sep. 20, 2004, now U.S. Pat. No. 7,837,729, and Ser. No. 10/945,855, filed Sep. 20, 2004, now U.S. Pat. No. 8,182,529.

An exemplary method of performing mitral valve annuloplasty on a patient's heart is described. As indicated above, the intravascular device is preferably loaded into and delivered to a desired location within a catheter with the proximal and distal anchors in a delivery or collapsed condition. Medical personnel may deploy the distal end of the intravascular device from the catheter into the lumen of a coronary sinus by advancing the intravascular device or by retracting the catheter, or a combination thereof. A delivery tool such as that of FIG. 7 may provide for distal movement of the intravascular device with respect to the catheter, and a tether may provide proximal movement of the device or for maintaining the position of the intravascular device relative to distal motion of a catheter. Because of the inherent recoverability of the material from which it is formed, the distal anchor begins to expand as soon as it is deployed from the catheter. Using the delivery tool, the distal loop of the distal anchor is moved distally so that the distal anchor further expands and locks in place to securely engage the coronary sinus wall and remains in the locked expanded configuration. The vessel may exert a compressive force on the distal part of the distal anchor, due to, for example, the narrowing diameter of the vessel. The distal anchor as adapted resists compression of the distal part therefore resisting expansion of a proximal part in response to this compressive force. In addition, the greater width of the distal anchor in comparison to its height helps create strain on the vessel to increase the anchoring action.

Next, the intravascular device is tensioned by pulling on the tether to apply a proximally-directed cinching force on the distal anchor, thereby modifying the shape of the coronary sinus and adjacent nearby valve annulus tissue. Fluoroscopy, ultrasound or other imaging technology may be used to detect when the device modifies the shape of the mitral valve annulus sufficiently to reduce mitral valve regurgitation without otherwise adversely affecting the patient. A preferred method of assessing efficacy and safety during a mitral valve procedure is disclosed in U.S. patent application Ser. No. 10/366,585, filed Feb. 12, 2003. Once the device has been sufficiently cinched, the proximal anchor is deployed from the catheter to begin expansion. In some embodiments, the proximal anchor is deployed in the coronary sinus, but it may be deployed in other vessels as well. The proximal loop of the proximal anchor is advanced distally over the arrowhead-shaped element by the delivery tool to further expand and lock the proximal anchor, thus engaging the coronary sinus wall or other vessel and maintaining a cinching force of the device on the mitral valve annulus. Finally, the coupler that couples the intravascular device to a delivery tool can be released. A hitch wire is first withdrawn (by, for example, a hitch wire actuator of the delivery tool of FIG. 7), thereby releasing the loop so it can be pulled through the proximal lock, and thereby uncoupling the intravascular device from the delivery tool.

In some embodiments it may be necessary to move or remove the intravascular device after deployment by recapturing the device into a catheter. After the distal anchor is deployed and prior to initial deployment of the proximal anchor, the distal anchor may be recaptured into the delivery catheter by holding the intravascular device in place with a the tether while advancing the catheter distally over the distal anchor so that the entire intravascular device is once again inside the catheter. The distally directed force of the catheter collapses the distal anchor to ease recapture into the catheter. In some embodiments the tether may be used to pull the intravascular device proximally while holding the catheter stationary. Either motion, or a combination of motions, may be used to recapture the distal anchor. Similarly, after deploying the second anchor but prior to releasing the coupler as described above herein, the intravascular device may be captured into the delivery catheter by holding the device in place with the tether while advancing a catheter distally first over a proximal anchor, over the support structure, and finally over a distal anchor. The distally directed force of the catheter collapses the anchors such that they can again fit within the catheter. The tether may also be used to pull the device proximally while holding the catheter stationary. If the coupler has been detached from the device prior to capture, the device may be recaptured into the delivery catheter or another catheter by grasping the proximal end of the device with a tether or grasper and by advancing the catheter distally over the device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

FIGS. 8-19 show embodiments of the device of this invention having flexible and expandable wire anchors which permit the delivery of tissue shaping devices 60 mm or less in length by a ten french (or less) catheter. In some embodiments, one or both of the anchors are provided with bending points about which the anchors deform when placed in their unexpanded configuration for delivery by a catheter or recapture into a catheter. These bending points enable the anchors to deform into configurations that minimize overlap with other elements of the device. In other embodiments, the distal anchor is self-expanding, thereby avoiding the need for a proximally-extending eyelet in the anchor's unexpanded configuration that might overlap with the unexpanded proximal anchor within the delivery and/or recapture catheter.

Figure 8:
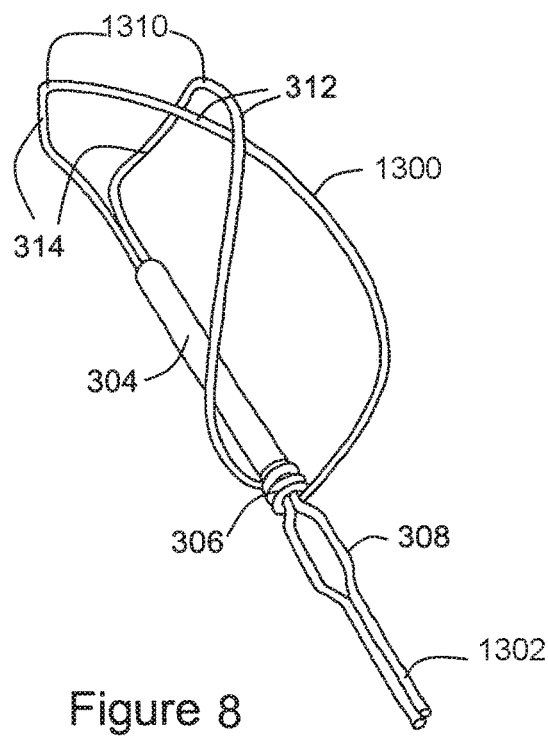
FIG. 8 illustrates one embodiment of a tissue shaping device in accordance with the present invention external to a patient's body. That is, the anchors are shown in expanded configurations and in the absence of bodily forces acting on the anchors. The tissue shaping device 100 includes a connector or support wire 102 having a proximal end 104 and a distal end 106. The support wire 102 is made of a biocompatible material such as stainless steel or a shape memory material such as nitinol wire.
Figure 9:
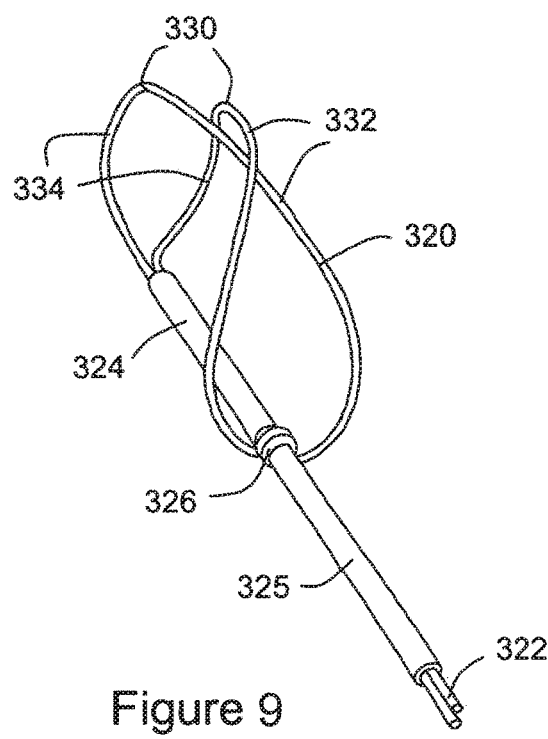
FIG. 9 is a partial sectional view of the tissue shaping device of FIG. 8 in an unexpanded configuration within a catheter.

FIG. 8 shows an actuatable anchor design suitable for a shorter tissue shaping device similar to the device shown in FIGS. 8 and 9. In this embodiment, distal anchor 1300 is disposed distal to a connector 1302. As in the embodiment of FIG. 8, anchor 1300 is formed in a figure eight configuration from flexible wire such as nitinol held by a crimp tube 304. An eyelet 306 is formed around the longitudinal axis of connector 1302. A distally directed actuation force on eyelet 306 moves it over a lock bump 308 formed in connector 1302 to actuate and lock anchor 1300.

FIG. 8 shows anchor 1300 in an expanded configuration. In an unexpanded configuration, such as a configuration suitable for loading anchor 1300 and the rest of the tissue shaping device into a catheter for initial deployment to treat mitral valve regurgitation, eyelet 306 is disposed proximal to lock bump 308, and the figure eight loops of anchor 1300 are compressed against crimp 304. In order to limit the proximal distance eyelet 306 must be moved along the connector to compress anchor 1300 into an unexpanded configuration, bending points 1310 are formed in the distal struts of anchor 1300. Bending points 1310 are essentially kinks, i.e., points of increased curvature, formed in the wire. When anchor 1300 is compressed into an unexpanded configuration, bending points 1310 deform such that the upper arms 312 of the distal struts bend around bending points 1310 and move toward the lower arms 314 of the distal struts, thereby limiting the distance eyelet 306 and the anchor's proximal struts must be moved proximally along the connector to compress the anchor.

Likewise, if distal anchor were to be recaptured into a catheter for redeployment or removal from the patient, anchor 1300 would deform about bending points 1310 to limit the cross-sectional profile of the anchor within the catheter, even if eyelet 306 were not moved proximally over lock bump 308 during the recapture procedure. Bending points may also be provided on the proximal anchor in a similar fashion.

As stated above, distal anchor 1300 may be part of a tissue shaping device (such as that shown in FIGS. 8 and 9) having a proximal anchor and a connector disposed between the anchors. To treat mitral valve regurgitation, distal anchor 1300 may be deployed from a catheter and expanded with an actuation force to anchor against the coronary sinus wall to provide an anchoring force of at least one pound, preferably at least two pounds, and to lock anchor 1300 in an expanded configuration. A proximally directed force is applied to distal anchor 1300 through connector 1302, such as by moving the proximal anchor proximally about 1-6 cm, more preferably at least 2 cm, by pulling on a tether or control wire operated from outside the patient. The proximal anchor may then be deployed to maintain the reshaping force of the device.

One aspect of anchor 1300 is its ability to conform and adapt to a variety of vessel sizes. For example, when anchor 1300 is expanded inside a vessel such as the coronary sinus, the anchor's wire arms may contact the coronary sinus wall before the eyelet 306 has been advanced distally over lock bump 308 to lock the anchor in place. While continued distal advancement of eyelet 306 will create some outward force on the coronary sinus wall, much of the energy put into the anchor by the anchor actuation force will be absorbed by the deformation of the distal struts about bending points 1310, which serve as expansion energy absorption elements and thereby limit the radially outward force on the coronary sinus wall. This feature enables the anchor to be used in a wider range of vessel sizes while reducing the risk of over-expanding the vessel.

FIG. 9 shows another anchor design in which distal anchor 320 is disposed distal to a connector 322. Anchor 320 is formed in a figure eight configuration from flexible wire such as nitinol held by a crimp tube 324. Unlike the embodiment of FIG. 8, however, anchor 320 is self-expanding and is not actuatable. Eyelet 326 is held in place by a second crimp 325 to limit or eliminate movement of the anchor's proximal connection point proximally or distally, e.g., along connector 322.

FIG. 9 shows anchor 320 in an expanded configuration. In an unexpanded configuration, such as a configuration suitable for loading anchor 320 and the rest of the tissue shaping device into a catheter for initial deployment to treat mitral valve regurgitation, the figure eight loops of anchor 320 are compressed. Bending points 330 are formed in the distal struts of anchor 320. When anchor 320 is compressed into an unexpanded configuration, bending points 330 deform such that the upper arms 332 of the distal struts bend around bending points 330 and move toward the lower arms 334 of the distal struts. Depending upon the exact location of bending points 330, very little or none of the wire portion of anchor 320 is disposed proximally along crimp 325 or connector 322 when anchor 320 is in its unexpanded configuration.

Likewise, if distal anchor were to be recaptured into a catheter for redeployment or removal from the patient, anchor 320 would deform about bending points 330 to limit the cross-sectional profile of the anchor within the catheter. Bending points may also be provided on the proximal anchor in a similar fashion.

Distal anchor 320 may be part of a tissue shaping device having a proximal anchor and a connector disposed between the anchors. Due to the superelastic properties of its shape memory material, distal anchor 320 may be deployed from a catheter to self-expand to anchor against the coronary sinus wall to provide an anchoring force of at least one pound, preferably at least two pounds. A proximally directed force may then be applied to distal anchor 320 through connector 322, such as by moving the proximal anchor proximally about 1-6 cm, more preferably at least 2 cm, by pulling on a tether or control wire operated from outside the patient. The proximal anchor may then be deployed to maintain the reshaping force of the device.

Figure 10:
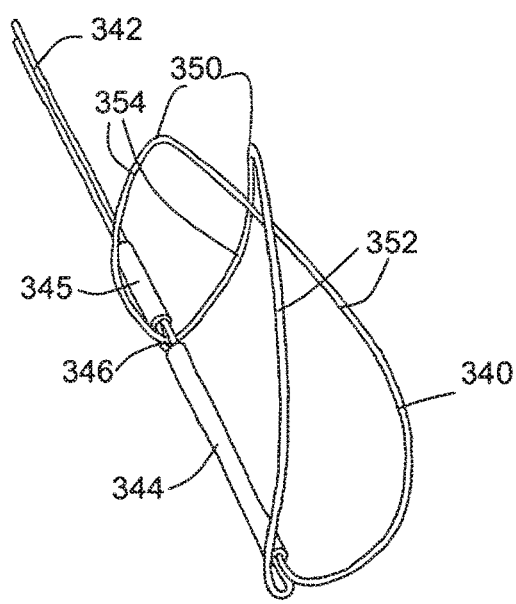
FIG. 10 is a perspective view of an anchor for use with a tissue shaping device according to this invention.

FIG. 10 shows another embodiment of an anchor suitable for use in a shorter tissue shaping device. In this embodiment, distal anchor 340 is disposed distal to a connector 342. As in the embodiment of FIG. 9, anchor 340 is formed in a figure eight configuration from flexible wire such as nitinol held by a crimp tube 344. Also like that embodiment, anchor 340 is self-expanding and is not actuatable. The loop of anchor 340 forming the anchor's proximal struts passes through a loop 346 extending distally from a second crimp 345 to limit or eliminate movement of the anchor's proximal struts proximally or distally, e.g., along connector 342.

FIG. 10 shows anchor 340 in an expanded configuration. Like the device of FIG. 9, in an unexpanded configuration, such as a configuration suitable for loading anchor 340 and the rest of the tissue shaping device into a catheter for initial deployment to treat mitral valve regurgitation, the figure eight loops of anchor 340 are compressed. Unlike the FIG. 9 embodiment, however, bending points 350 are formed in the proximal struts of anchor 340. When anchor 340 is compressed into an unexpanded configuration, bending points 350 deform such that the upper arms 352 of the distal struts bend around bending points 350 and move toward the lower arms 354 of the distal struts. The amount of the wire portion of anchor 340 extending proximally along crimp 345 and connector 342 in its unexpanded configuration depends on the location of bending points 350. In one embodiment, the bending points are formed at the tallest and widest part of the proximal struts.

Distal anchor 340 may be part of a tissue shaping device having a proximal anchor and a connector disposed between the anchors. Due to the superelastic properties of its shape memory material, distal anchor 340 may be deployed from a catheter to self-expand to anchor against the coronary sinus wall to provide an anchoring force of at least one pound, preferably at least two pounds. A proximally directed force may then be applied to distal anchor 340 through connector 342, such as by moving the proximal anchor proximally about 1-6 cm, more preferably at least 2 cm, by pulling on a tether or control wire operated from outside the patient. The proximal anchor may then be deployed to maintain the reshaping force of the device.

Bending points 350 also add to the anchoring force of distal anchor 340, e.g., by causing the anchor height to increase as the proximal struts become more perpendicular to the connector in response to a proximally directed force, thereby increasing the anchoring force. In the same manner, bending points may be added to the distal struts of a proximal anchor to increase the proximal anchor's anchoring force in response to a distally directed force.

Figure 11:
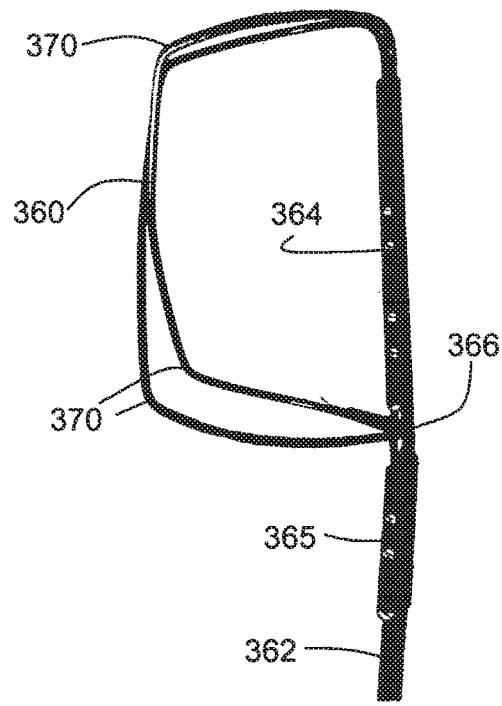
FIG. 11 is a perspective view of another anchor for use with a tissue shaping device according to this invention.

FIG. 11 shows yet another embodiment of an anchor suitable for use in a shorter tissue shaping device. In this embodiment, distal anchor 360 is disposed distal to a connector 362. As in the embodiment of FIG. 12, anchor 360 is formed in a figure eight configuration from flexible wire such as nitinol held by a crimp tube 364. Also like that embodiment, anchor 360 is self-expanding and is not actuatable. The loop of anchor 360 forming the anchor's proximal struts passes through a loop 366 extending distally from a second crimp 365 to limit or eliminate movement of the anchor's proximal struts proximally or distally, e.g., along connector 362.

FIG. 11 shows anchor 360 in an expanded configuration. Like the device of FIG. 10, in an unexpanded configuration, such as a configuration suitable for loading anchor 360 and the rest of the tissue shaping device into a catheter for initial deployment to treat mitral valve regurgitation, the figure eight loops of anchor 360 are compressed. Unlike the FIG. 10 embodiment, however, bending points 370 are formed in both the proximal struts and the distal struts of anchor 360.

Anchor 360 may be used as part of a tissue shaping device like the embodiments discussed above.

Figure 12:
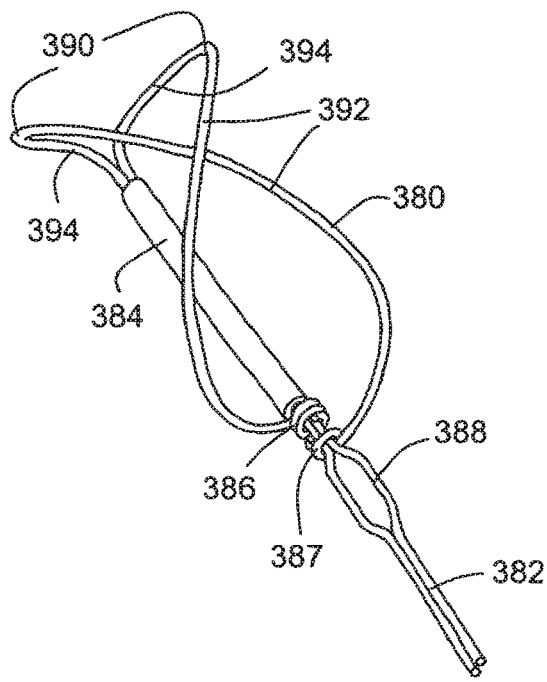
FIG. 12 is a perspective view of yet another anchor for use with a tissue shaping device according to this invention.

FIG. 12 shows an actuatable anchor design suitable for a shorter tissue shaping device. In this embodiment, distal anchor 380 is disposed distal to a connector 382. As in the other embodiments, anchor 380 is formed in a figure eight configuration from flexible wire such as nitinol held by a crimp tube 384. In contrast to the embodiment of FIG. 8, eyelets 386 and 387 are formed in each of the anchor's proximal struts around the longitudinal axis of connector 382. This arrangement reduces the radially outward force of the anchor. A distally directed actuation force on eyelets 386 and 387 move them over a lock bump 388 formed in connector 382 to actuate and lock anchor 380.

FIG. 12 shows anchor 380 in an expanded configuration. In an unexpanded configuration, such as a configuration suitable for loading anchor 380 and the rest of the tissue shaping device into a catheter for initial deployment to treat mitral valve regurgitation, eyelets 386 and 387 are disposed proximal to lock bump 388 and the figure eight loops of anchor 380 are compressed against crimp 384. In order to limit the proximal distance eyelets 386 and 387 must be moved to compress anchor 380 into an unexpanded configuration, bending points 390 are formed in the distal struts of anchor 380. When anchor 380 is compressed into an unexpanded configuration, bending points 390 deform such that the upper arms 392 of the distal struts bend around bending points 390 and move toward the lower arms 394 of the distal struts, thereby limiting the distance eyelets 386 and 387 and the anchor's proximal struts must be moved proximally along the connector to compress the anchor.

If distal anchor were to be recaptured into a catheter for redeployment or removal from the patient, anchor 380 would deform about bending points 390 to limit the cross-sectional profile of the anchor within the catheter, even if eyelets 386 and 387 were not moved proximally over lock bump 388 during the recapture procedure. Bending points may also be provided on the proximal anchor in a similar fashion.

As with the other embodiments above, distal anchor 380 may be part of a tissue shaping device having a proximal anchor and a connector disposed between the anchors. To treat mitral valve regurgitation, distal anchor 380 may be deployed from a catheter and expanded with an actuation force to anchor against the coronary sinus wall to provide an anchoring force of at least one pound, preferably at least two pounds, and to lock anchor 380 in an expanded configuration. A proximally directed force is applied to distal anchor 380 through connector 382, such as by moving the proximal anchor proximally about 1-6 cm, more preferably at least 2 cm, by pulling on a tether or control wire operated from outside the patient. The proximal anchor may then be deployed to maintain the reshaping force of the device.

As with other embodiments, one aspect of anchor 380 is its ability to conform and adapt to a variety of vessel sizes. For example, when anchor 380 is expanded inside a vessel such as the coronary sinus, the anchor's wire arms may contact the coronary sinus wall before the eyelets 386 and 387 have been advance distally over lock bump 388 to lock the anchor in place. While continued distal advancement of eyelet 386 will create some outward force on the coronary sinus wall, much of the energy put into the anchor by the anchor actuation force will be absorbed by the deformation of the distal struts about bending points 390.

Figure 13:
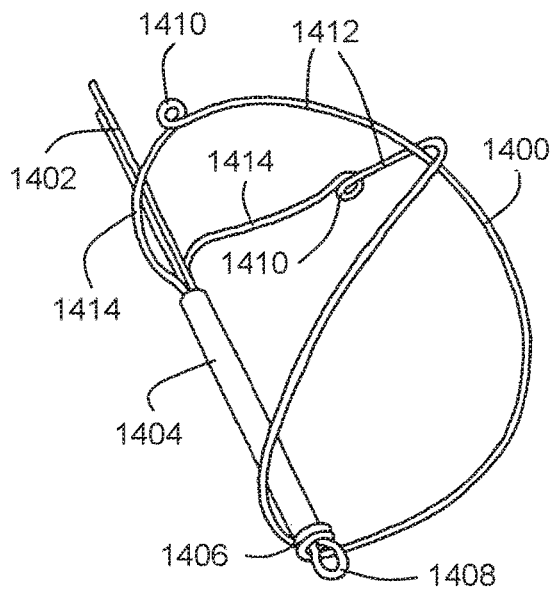
FIG. 13 is a perspective view of still another anchor for use with a tissue shaping device according to this invention.

FIG. 13 shows yet another embodiment of an actuatable anchor for use in a shorter tissue shaping device. Proximal anchor 1400 is disposed proximal to a connector 1402. As in other embodiments, anchor 1400 is formed in a figure eight configuration from flexible wire such as nitinol held by a crimp tube 1404. An eyelet 1406 is formed around a lock bump 408 extending proximally from crimp 1404. A distally directed actuation force on eyelet 406 moves it over lock bump 1408 to actuate and lock anchor 400.

FIG. 13 shows anchor 1400 in an expanded configuration. When anchor 1400 is compressed into an unexpanded configuration, bending points 1410 formed as loops in the anchor wire deform such that the upper arms 1412 of the distal struts bend around bending points 1410 and move toward the lower arms 1414 of the distal struts. As with the other embodiments, proximal anchor 1400 may be part of a tissue shaping device (such as that shown in FIGS. 8 and 9) having a distal anchor and a connector disposed between the anchors.

Like other embodiments, one aspect of anchor 1400 is its ability to conform and adapt to a variety of vessel sizes. For example, when anchor 1400 is expanded inside a vessel such as the coronary sinus, the anchor's wire arms may contact the coronary sinus wall before the eyelet 1406 has been advanced distally over lock bump 1408 to lock the anchor in place. While continued distal advancement of eyelet 1406 will create some outward force on the coronary sinus wall, much of the energy put into the anchor by the anchor actuation force will be absorbed by the deformation of the distal struts about bending points 1410, which serve as expansion energy absorption elements and thereby limit the radially outward force on the coronary sinus wall.

Figure 14:
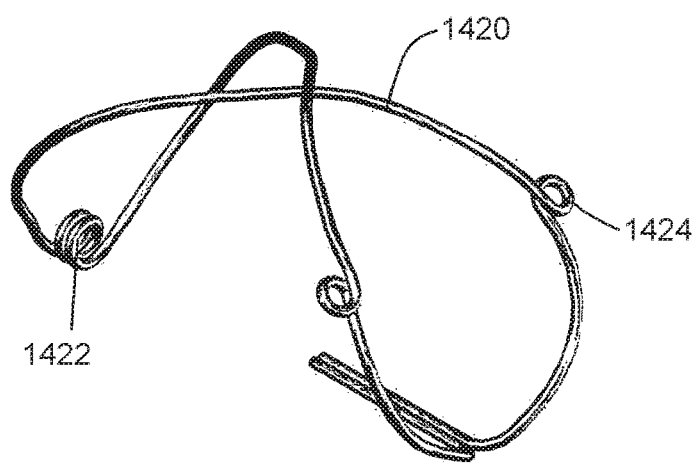
FIG. 14 is a perspective view of another anchor for use with a tissue shaping device according to this invention.

In other embodiments, the looped bending points of the FIG. 13 embodiment may be formed on the anchor's proximal struts in addition to or instead of on the distal struts. The looped bending point embodiment may also be used in a distal anchor, as shown in FIG. 14 (without the crimp or connector). Note that in the embodiment of FIG. 14 the proximal and distal struts of anchor 1420 as well as the eyelet 1422 and bending points 1424 are formed from a single wire.

Figure 15:
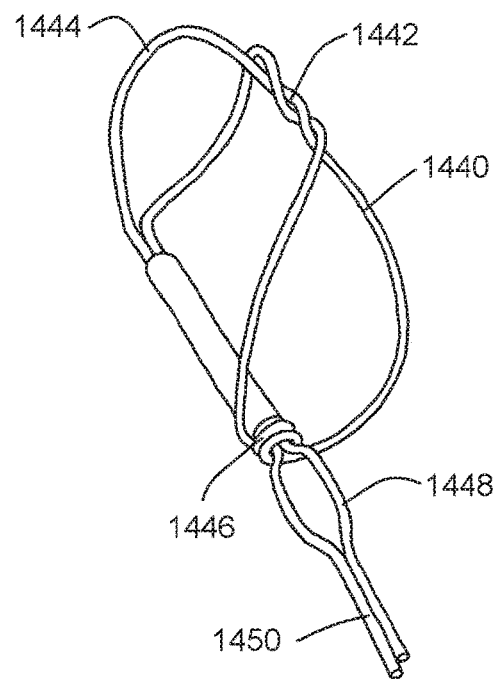
FIG. 15 is a perspective view of yet another anchor for use with a tissue shaping device according to this invention.

FIG. 15 shows an embodiment of a distal anchor 1440 similar to that of FIG. 8 suitable for use in a shorter tissue shaping device. In this embodiment, however, extra twists 1442 are added at the apex of the anchor's figure eight pattern. As in the FIG. 8 embodiment, bending points 1444 are formed in the anchor's distal struts. As shown, anchor 1440 is actuatable by moving eyelet 1446 distally over a lock bump 1448 formed in connector 1450. Anchor 1440 may also be made as a self-expanding anchor by limiting or eliminating movement of the proximal struts of anchor 1440 along connector 1450, as in the embodiment shown in FIG. 9. As with other embodiments, the bending points help anchor 1440 adapt and conform to different vessel sizes. In addition, the extra twists 1442 also help the anchor adapt to different vessel diameters by keeping the anchor's apex together.

As in the other embodiments, anchor 1440 is preferably formed from nitinol wire. Anchor 1440 may be used as part of a tissue shaping device. Anchor 1440 may also be used as a proximal anchor.

Figure 16:
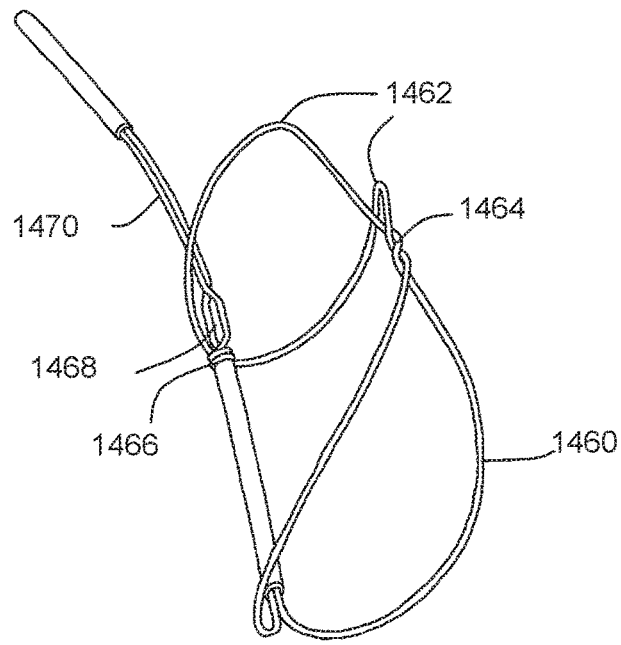
FIG. 16 is a perspective view of part of an anchor for use with a tissue shaping device according to this invention.

FIG. 16 shows an embodiment of a distal anchor 1460 similar to that of FIG. 15. In this embodiment, however, the bending points 1462 are formed in the anchor's proximal struts, as in the self-expanding anchor shown in FIG. 12. As in the FIG. 15 embodiment, extra twists 1464 are added at the apex of the anchor's figure eight pattern. As shown, anchor 1460 is actuatable by moving eyelet 1466 distally over a lock bump 1468 formed in connector 1470. Anchor 1460 may also be made as a self-expanding anchor by limiting or eliminating movement of the proximal connection point of anchor 1460 along connector 1470, as in the embodiment shown in FIG. 9. As with the embodiment of FIG. 15, the bending points help anchor 1460 adapt and conform to different vessel sizes. In addition, the extra twists 1464 also help the anchor adapt to different vessel diameters by keeping the anchor's apex together.

As in the other embodiments, anchor 1460 is preferably formed from nitinol wire. Anchor 1460 may be used as part of a tissue shaping device in a manner similar to the anchor of FIG. 8 (for the actuatable anchor embodiment) or the anchor of FIG. 9 (for the self-expanding anchor embodiment). Anchor 1460 may also be used as a proximal anchor.

Figure 17:
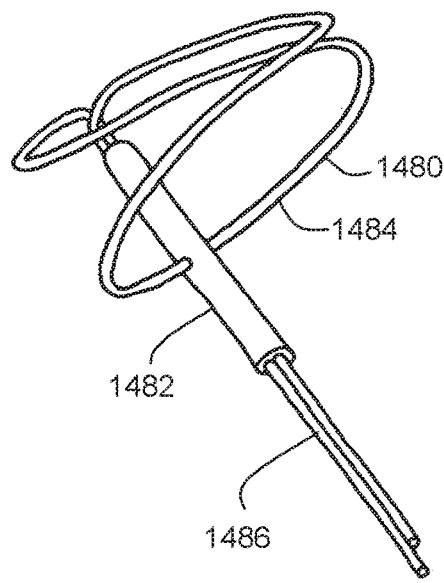
FIG. 17 is a perspective view of still another anchor for use with a tissue shaping device according to this invention.

FIG. 17 shows an embodiment of a self-expanding distal anchor 1480 suitable for use in a shorter tissue shaping device. As in the other embodiments, anchor 1480 is formed in a figure eight configuration from flexible wire such as nitinol held by a crimp tube 1482. The base of the figure eight pattern is narrower in this embodiment, however, with the anchor's proximal struts 1484 passing through crimp 1482.

Distal anchor 1480 may be part of a tissue shaping device having a proximal anchor and a connector disposed between the anchors. To treat mitral valve regurgitation, distal anchor 1480 may be deployed from a catheter and allowed to self-expand to anchor against the coronary sinus wall to provide an anchoring force of at least one pound, preferably at least two pounds. A proximally directed force is applied to distal anchor 1480 through connector 1486, such as by moving the proximal anchor proximally about 1-6 cm, more preferably at least 2 cm, by pulling on a tether or control wire operated from outside the patient. The proximal anchor may then be deployed to maintain the reshaping force of the device.

Figure 18:
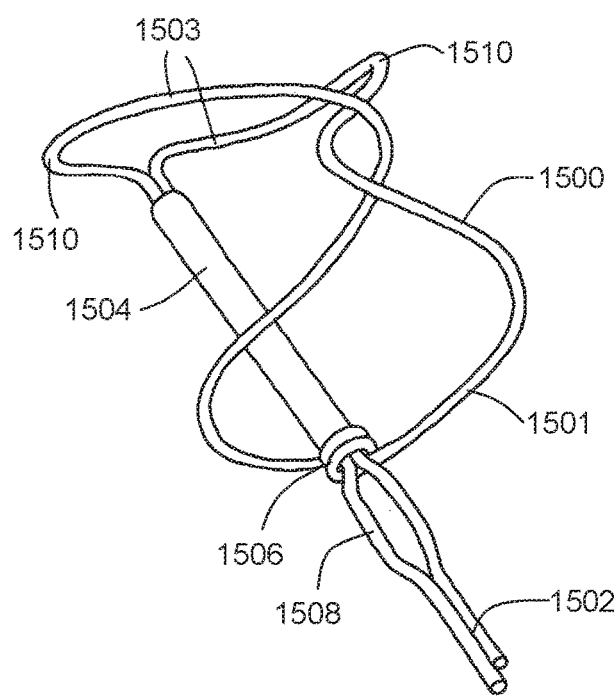
FIG. 18 is a perspective view of another anchor for use with a tissue shaping device according to this invention.
Figure 19:
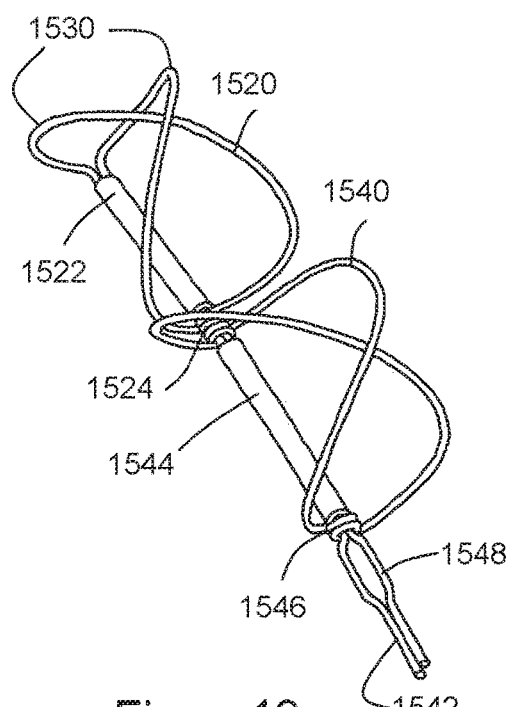
FIG. 19 is a perspective view of yet another anchor for use with a tissue shaping device according to this invention.

FIG. 18 shows an embodiment of a distal anchor suitable for use in a shorter tissue shaping device and similar to that of FIG. 8. In this embodiment, distal anchor 1500 is disposed distal to a connector 1502. As in other embodiments, anchor 1500 is formed in a figure eight configuration from flexible wire such as nitinol held by a crimp tube 1504. An eyelet 1506 is formed around the longitudinal axis of connector 1502. A distally directed actuation force on eyelet 1506 moves it over a lock bump 1508 formed in connector 1502 to actuate and lock anchor 1500.

The angle of proximal struts 1501 and the angle of distal struts 1503 are wider than corresponding angles in the FIG. 8 embodiment, however, causing anchor 1500 to distend more in width than in height when expanded, as shown. In an unexpanded configuration, such as a configuration suitable for loading anchor 1500 and the rest of the tissue shaping device into a catheter for initial deployment to treat mitral valve regurgitation, eyelet 1506 is disposed proximal to lock bump 1508 and the figure eight loops of anchor 1500 are compressed against crimp 1504. In order to limit the proximal distance eyelet 1506 must be moved along the connector to compress anchor 1500 into an unexpanded configuration, bending points 1510 are formed in the distal struts 1503, as in the FIG. 8 embodiment, to limit the width of the device in its unexpanded configuration within a catheter.

Distal anchor 1500 may be part of a tissue shaping device having a proximal anchor and a connector disposed between the anchors. To treat mitral valve regurgitation, distal anchor 1500 may be deployed from a catheter and expanded with an actuation force to anchor against the coronary sinus wall to provide an anchoring force of at least one pound, preferably at least two pounds, and to lock anchor 1500 in an expanded configuration. A proximally directed force is applied to distal anchor 1500 through connector 1502, such as by moving the proximal anchor proximally about 1-6 cm, more preferably at least 2 cm, by pulling on a tether or control wire operated from outside the patient. The proximal anchor may then be deployed to maintain the reshaping force of the device.

The anchor shown in FIG. 18 may be used as a proximal anchor. This anchor may also be formed as a self-expanding anchor.

What is claimed is:

1. A mitral valve therapy device, the therapy device comprising:
   an expandable first anchor, an expandable second anchor, and an elongate body extending therebetween, the expandable first anchor having an anchored configuration,
   the expandable first anchor comprising a first segment and a second segment, the first segment extending from a distal end of the first anchor to a proximal end of the first anchor, the second segment extending from a distal end of the first anchor to a proximal end of the first anchor, and in the anchored configuration the first segment engages the second segment in an axially central location between the distal end of the first anchor and the proximal end of the first anchor to form at least one full twist around the second segment in which the first segment passes over the second segment and then under the second segment and in which the second segment passes under the first segment and then over the first segment.

2. The device of claim 1, wherein the expandable first anchor further comprises a securing member for securing an end of the first segment and an end of the second segment therein at a distal end of the securing member, the securing member generally aligned with the elongate body.

3. The device of claim 2, wherein the first segment forms a loop around the elongate body proximal to the securing member, and the second segment extends from the loop to the distal end of the expandable first anchor.

4. The device of claim 2, wherein the elongate body extends into a proximal end of the securing member.

5. The device of claim 1, further comprising a lock that locks the expandable first anchor in the anchored configuration.

6. The device of claim 1, wherein the expandable first anchor is adapted to self-expand when deployed from a delivery member.

7. The device of claim 1, wherein the first and second segments each comprise a bending region formed therein at a region of increased curvature that is configured such that the first and second segments preferentially bend at the bending regions during expansion and collapse.

8. The device of claim 1, wherein the expandable second anchor has an anchored configuration, the expandable second anchor comprising a second anchor first segment and a second anchor second segment, and in the anchored configuration of the expandable second anchor the second anchor first segment engages the second anchor second segment to form at least one full twist around the second anchor second segment in a central portion of the expandable second anchor in which the second anchor first segment passes over the second anchor second segment and then under the second anchor second segment and in which the second anchor second segment passes under the second anchor first segment and then over the second anchor first segment.

* * * * *